United States Patent [19]
Dougherty et al.

[11] Patent Number: 6,143,565
[45] Date of Patent: Nov. 7, 2000

[54] STABLE INSECT VIRUS-CELL EXPRESSION SYSTEM

[75] Inventors: Edward M. Dougherty, Alexandria, Va.; Terry A. McKelvey, Gaithersburg, Md.; Donald A. Stoltz, Halifax, Canada; Dwight E. Lynn, Severn; Dawn E. Gundersen-Rindal, Silver Spring, both of Md.

[73] Assignee: The United States of America as represented by the Secretary of Agriculture, Washington, D.C.

[21] Appl. No.: 08/916,265

[22] Filed: Aug. 22, 1997

[51] Int. Cl.[7] .............................. C12N 15/87; C12N 5/10
[52] U.S. Cl. .......................... 435/456; 435/455; 435/348; 435/235.1
[58] Field of Search .............................. 435/235.1, 320.1, 435/172.3, 348, 948, 455, 456; 536/23.72, 24.2, 24.32

[56] References Cited

PUBLICATIONS

Strand et al. Archives of Insect Biochemistry and Physiology 18 (3): 131–146 (abstract only), 1991.

Stoltz et al. Canadian Journal of Microbiology 36: 538–543, 1990.

Xu et al, Journal of Virology 65: 6693–6704, 1991.

McKelvey et al., *Biochemical and Biophysical Research Communications,* vol. 225(3), Article No. 1248, p. 764–770(1996).

Kim et al., *Journal of General Virology,* vol. 77, p. 2321–2328(1996).

Gundersen–Rindal et al., Abstracts, *Asilomar 1997,* Second International Workshop on Transgenesis of Invertebrate Organisms, May 9–13, 1997.

*Primary Examiner*—Mary E. Mosher
*Attorney, Agent, or Firm*—M. Howard Silverstein; John D. Fado; Janelle S. Graeter

[57] ABSTRACT

A stable transformed insect cell line has been achieved by infecting an insect cell culture with fluid obtained from a female parasitoid wasp, such as *Glyptapanteles indiensis*. The fluid contains polydnavirus DNA capable of integrating into the host cell genome. Susceptible insect cells include both Lepidopteran and Coleopteran cells.

4 Claims, 9 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 19 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Glyptapanteles indiensis (xi) SEQUENCE DESCRIPTION: SEQ ID NO:1:

CTACGTCTAG CTTCTCAAG                                               19

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Glyptapanteles indiensis (xi) SEQUENCE DESCRIPTION: SEQ ID NO:2:

CATGATTAAT ACTGTAACAT C                                            21

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Glyptaneles indiensis (xi) SEQUENCE DESCRIPTION: SEQ ID NO:3:

CTACAAGATA CAGGTCAATC                                              20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Glytapanteles indiensis
```

```
        (xi) SEQUENCE DESCRIPTION: SEQ ID NO:4:

GCGGTGATGA CGTAGGTGAC                                                          20

(2) INFORMATION FOR SEQ ID NO:5:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Glyptapanteles indiensis/Lymantria dispar (xi) SEQUENCE DESCRIPTION: SEQ ID NO:5:

TTTAAATTTC GACAACGAGA AGGTACCATG TTACTTGCAG TCCTGTGTGA TGAAGGATTT              60
```

STABLE INSECT VIRUS-CELL EXPRESSION SYSTEM

BACKGROUND OF THE INVENTION

1. Field of the Invention

Systems for the stable transformation of insect cells have been pursued because of their potential to advance the fields of insect genetics, biochemistry, developmental biology, agriculture and medicine. Insect cell culture provides ideal conditions for the study and manipulation of insect genomes in vitro. Increased efforts have been made to isolate transposable and viral elements as vehicles for genetic transformation of insect cells and for use in biotechnology for gene expression in vitro. Thus far, routine gene transfer in insects has been possible only in members of the genus Drosophila (Handler and O'Brochta. 1991. *Ann. Rev. Entomol.* vol. 36, pp. 159–183), although methods have been sought for generalized transformation of other insect genomes. This invention relates to a segment of a polydnavirus genome which is capable of stable integration into the genome of an insect cell.

2. Description of the Related Art

Cell lines established from a number of insect species, predominantly from the orders Lepidoptera and Diptera [Lynn et al. 1988. In: *Invertebrate and fish tissue culture.* (Kuroda et al., eds) Japan Scientific Societies Press, Tokyo, pp. 239–242] facilitated the study of insect cellular physiology, endocrinology and biochemistry. Some cell lines have been utilized for studies on insect viruses and have shown varying susceptibilities to infection (Lynn et al., supra). In addition, the manipulation of insect viral replication in insect cells has proven useful. For example, the well-known baculovirus expression vector system (BEVS) has been used extensively for foreign gene expression in insect cells in vitro (King and Possee. 1992. *The baculovirus expression system.* Chapman & Hall, London), and other insect viruses have been investigated for potential utility as vectors for the introduction of genetic material into insect cell genomes in vitro (Giraud et al., 1992. *Virology.* vol. 186, pp. 207–218; McKelvey et al. 1996. *Biochem. and Biophys. Res. Comm. vol.* 225, pp. 764–770; Stoltz et al. 1986. *Virology.* vol. 155, pp. 120–131, all herein incorporated by reference).

Stable transformation of insect tissues, however, either in vivo or in vitro, has rarely been achieved (Ashburner, M. 1995. *Science.* vol. 270, pp. 1941–1942), especially the introduction of DNA into the germ line (Ashburner, supra). This event has been achieved thus far only in Drosophila (Rubin and Spradling. 1982. *Science.* vol. 218, pp. 348–353), by introduction of the P-element, and other transposable elements have recently been successfully used for transformation of the medfly, *Ceratitis capitata* (Loukeris et al. 1995. *Science.* vol. 270, pp. 2002–2003; Zweibel et al. 1995. *Science.* vol. 270, pp. 2005–2008). Because such transformation events require the injection of embryos, methods using viral vectors may be more useful.

Currently, the baculovirus expression system is the most commonly used system for the expression of foreign genes. Although this system is useful for both research and commercial purposes, it has a significant shortcoming, i.e. it can only express foreign genes transiently due to cell death from virus infection.

There is thus a need for a mechanism for the stable transformation of insect cells capable of the continuous expression of a desired protein.

SUMMARY OF THE INVENTION

We have discovered that a portion of the genome of polydnavirus of the parasitic wasp *Glyptapanteles indiensis* (*G. indiensis*) may be stably integrated into the genome of Lepidopteran and Coleopteran insect cell lines, resulting in a transformed insect cell line. Such cell lines may be used as models for the future development of stable transformation of foreign genes when inserted with the polydnavirus model systems, and as tools for developing viral-based insect-transforming vedtor. Such cell lines may be used for studying aberrant virus replication induced when those cells are challenged with baculoviruses and result in apotosis, interference and replicative anomalies. These data in turn can be used to understand the decreased effect baculoviruses have on parasitized *Lymantria dispar* (*L. dispar*).

In accordance with this discovery, it is an object of the invention to provide a portion of DNA capable of stably integrating into the genome of a Lepidopteran or a Coleopteran cell.

It is also an object of the invention to provide a transformed cell which has the DNA stably integrated into its genome.

It is a further object of the invention to provide a method of transforming an insect cell line with the DNA.

Other objects and advantages of the invention will become readily apparent from the following description.

BRIEF DESCRIPTION OF THE DRAWINGS

L. dispar cell lines, IPLB-Ld652Y, IPLB-LdEp and IPLB-LdEIta, were infected with polydnavirus. Lanes D, F and H contain BamHI digested genomic DNA from IPLB-Ld652Y, IPLB-LdEp and IPLB-LdEIta cells, respectively, not infected with GiPDV. Lanes E, G and I contain BamHI digested genomic DNA from IPLB-Ld652Y, IPLB-LdEp, and IPLB-LdEIta cells, respectively, infected with GiPDV. Lane J contains BamHI digested GiPDV DNA. Lanes A and B contain molecular standards indicated by size in kilobase pairs. Lanes C and K are blank.

FIG. 7 shows Southern blot analysis of G. indiensis genomic segment maintained in L. dispar cell lines. Genomic DNA (10 μg) from transformed and non-transformed IPLB-LdEp digested with BamHI or XbaI, undigested cellular, and uncut viral DNA was electrophoresed through a 0.7% agarose gel and transferred to nylon membrane. Digoxigenin-labeled DNA from a plasmid clone pTM145 was used as a hybridization probe. Lane C contains genomic DNA from uninfected IPLB-LdEp cells; lane D, genomic DNA fromn GiPDV infected IPLB-LdEp cells; lane E, uncut GiPDV DNA. Lanes F and H contain genomic DNA from GiPDV infected IPLB-LdEp cells digested with BamHI and XbaI, respectively. Lanes G and I contain GiPDV DNA digested with BamHI and XbaI, respectively. Lane A contains molecular size standard, indicated by size in kilobase pairs.

DETAILED DESCRIPTION OF THE INVENTION

Polydnaviruses are large complex multi-segmented DNA viruses with genomes consisting of a polydisperse mixture of circular double-stranded DNA molecules [Fleming and Krell. 1993. In: *Parasites and pathogens of insects.* (Bechage et al., eds.) Vol. 1, pp. 189–225. Academic Press, San Diego; Stoltz et al. 1984. *Intervirol.* vol. 21, p. 1]. These viruses are associated exclusively with certain species of Hymenopteran endoparasitic wasps. They are normally found integrated into the chromosome of Braconid or Ichneumonid parasitic wasp hosts and replicate only in the reproductive tract of the female wasps [Stoltz and Vinson. 1979a. *Advances in Virus Research.* vol. 24, pp. 125–171; Stoltz, D. B. 1993. In: *Parasites and pathogens of insects.* (Beckage et al., eds. Vol. 1, pp. 167–187, Academic Press, San Diego]. During parasitization, the viruses are injected with eggs, venom, and calyx fluid containing polydnavirus into their Lepidopteran host insects (Fleming and Summers. 1991. *Proc. Natl. Acad. Sci.* vol. 88, pp. 207–218; Gruber et al. 1996. *J. Gen. Virol.* vol. 77, pp. 2873–2879; Lavine and Beckage. 1995. *Parasitology Today.* vol. 11, pp. 368–378; Stoltz, D. B. 1993, supra). The virus subsequently infects a variety of host cells and tissues (Stoltz, and Vinson, supra; Stoltz and Vinson. 1979b. *Can. J. Microbiol.* vol. 25, pp. 207–216). The viruses do not replicate but disrupt the host immune system (Lavine and Beckage, supra).

A portion of braconid G. indiensis polydnavirus genome (GiPDV) is capable of integration into the insect host chromosome in vitro (McKelvey et al., supra) and is stably maintained. Because of its potential use in biotechnological applications, the host range of GiPDV was investigated (see Example 6). The results showed a wide range of lepidopteran cell lines permissive to GiPDV DNA. In addition to cells from its most important host insect L. dispar, or gypsy moth, also included are cells from three families (Lepidoptera, Coleoptera and Hymenoptera) which had been isolated from five different tissue sources. These included *Spodoptera frugiperda, Trichoplusia ni, Plodia interpunctella* and *Diabrotica undecimpunctata.* These insects do not normally encounter GiPDV in nature, but their cells are apparently susceptible to GiPDV infection in vitro, thus suggesting a very broad potential host range. A lack of GiPDV persistence was found in infected dipteran (mosquito) cells, however, indicating that there are limits to the GiPDV DNA host range.

Figure 1:
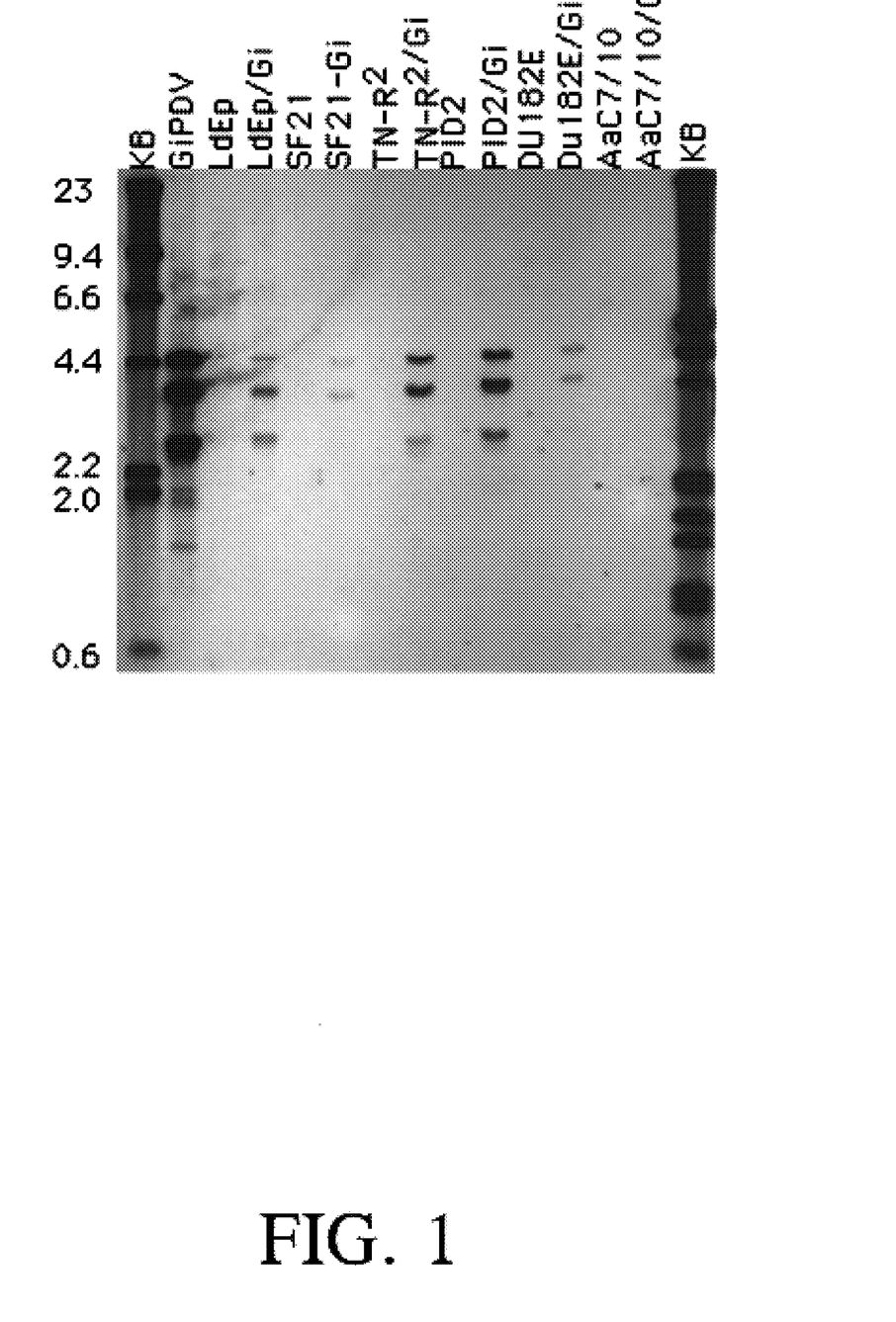
FIG. 1 shows a Southern blot analysis of GiPDV sequences maintained in insect cell lines. Genomic DNA from GiPDV, non-infected, and GiPDV-infected cell lines digested with EcoRI, was electrophoresed through a 0.8% agarose gel and transferred to nylon membrane. Digoxigenin-labeled DNA from clone pTM145 was used as a hybridization probe. Lanes contain EcoRI-digested genomic DNA from GiPDV, uninfected insect cells, or GiPDV-infected insect cells as labeled. Abbreviations are as given in Table 1. Molecular size standards are indicated in kilobase pairs.
Figure 2A:
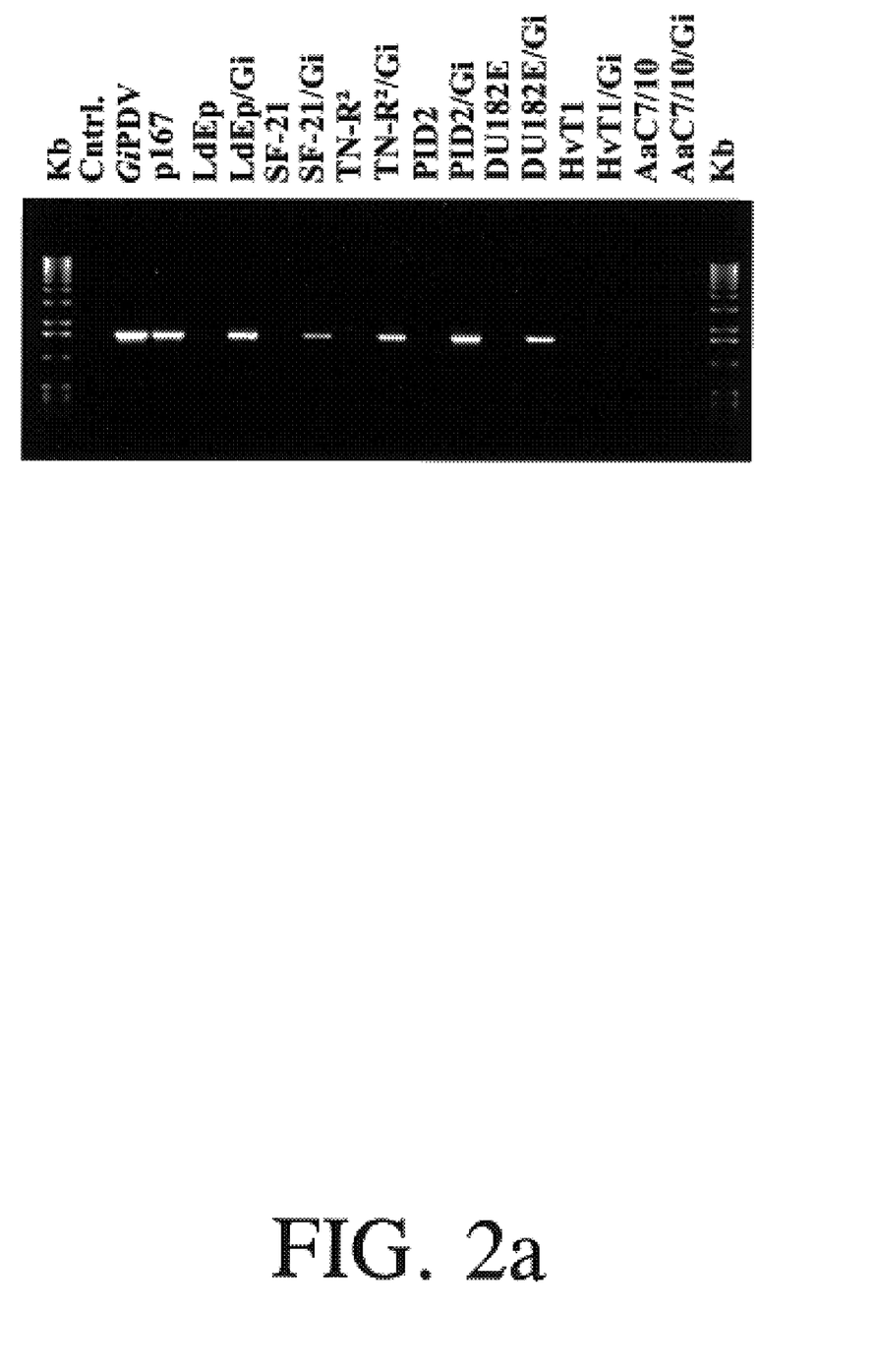
FIG. 2 shows results of polymerase chain reaction (PCR) amplification of GiPDV sequences from infected and non-infected insect cell line DNAs using GiPDV-specific primer pairs (A) p157F1/R1 and (B) p157F16/R16. Abbreviations are as given in Table 1. Lanes 1 and 19 contain molecular size standards indicated by size in kilobase pairs.
Figure 2B:
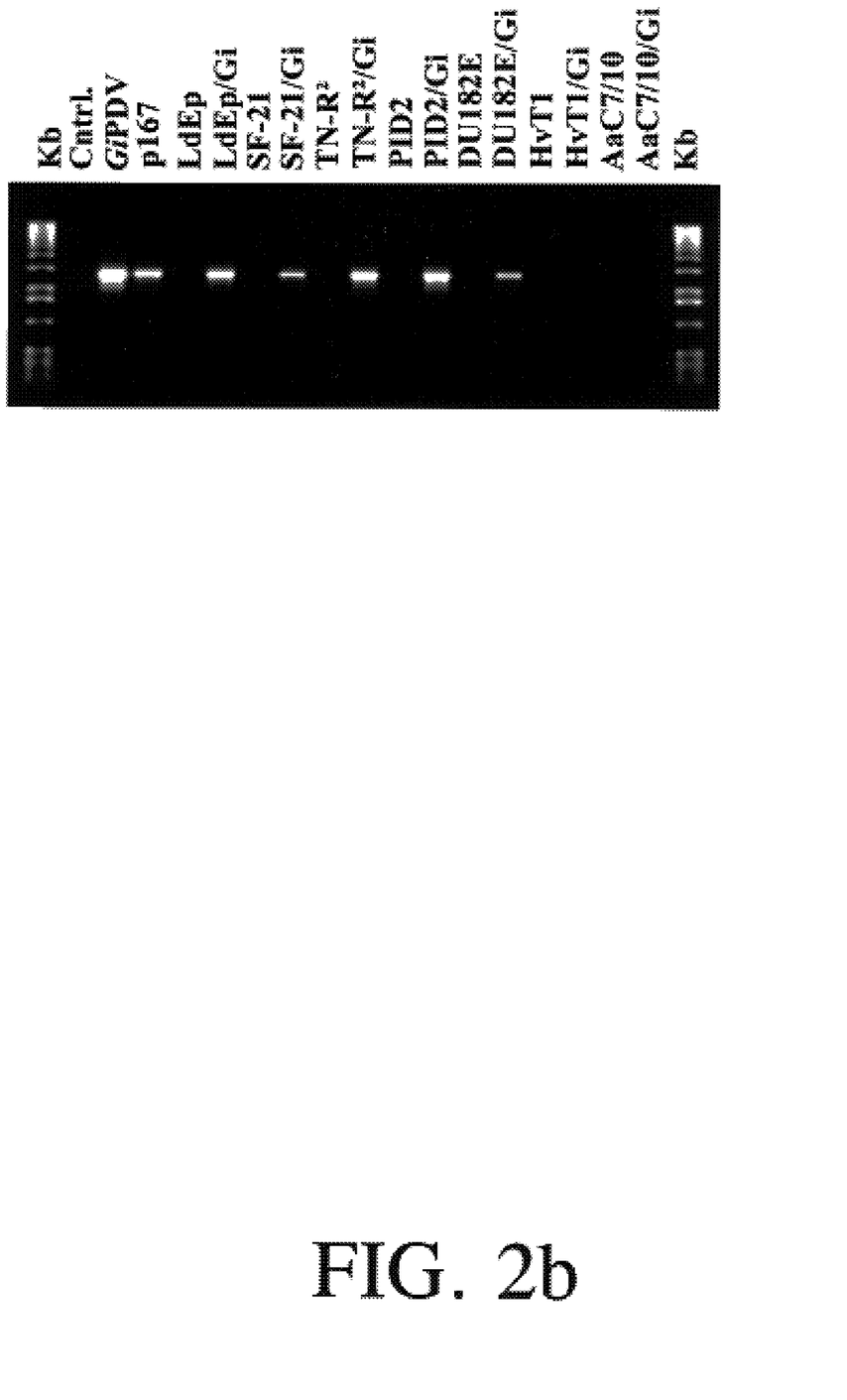
Figure 3:
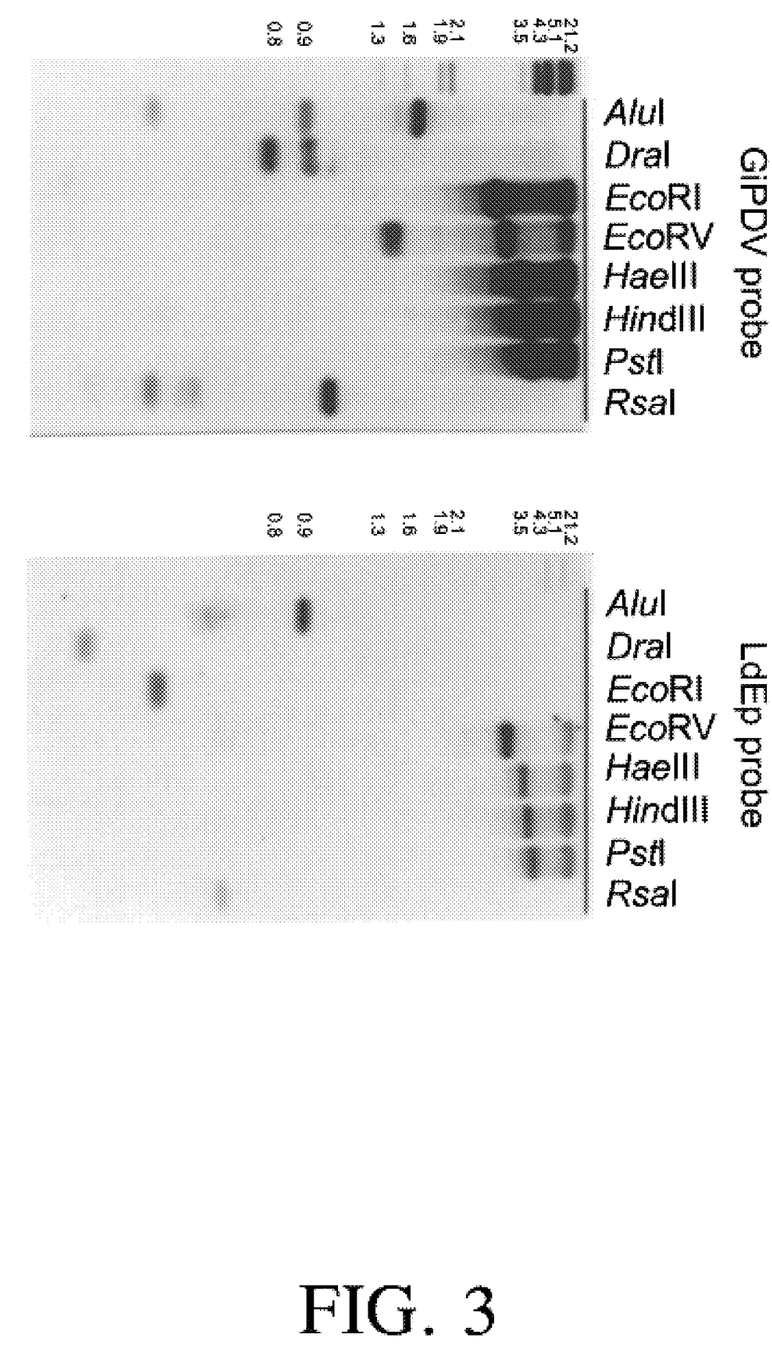
FIG. 3 shows Southern blot restriction analysis of clone p7-54. DNA (0.3 μg) from clone p7-54 was digested separately with restriction enzymes as labeled and electrophoresed through a 0.7% agarose gel and transferred to nylon membrane. Digoxigenin-labeled GiPDV virus and LdEp cellular DNAs were used separately as hybridization probes. Sizes are given in kilobase pairs.
Figure 4:
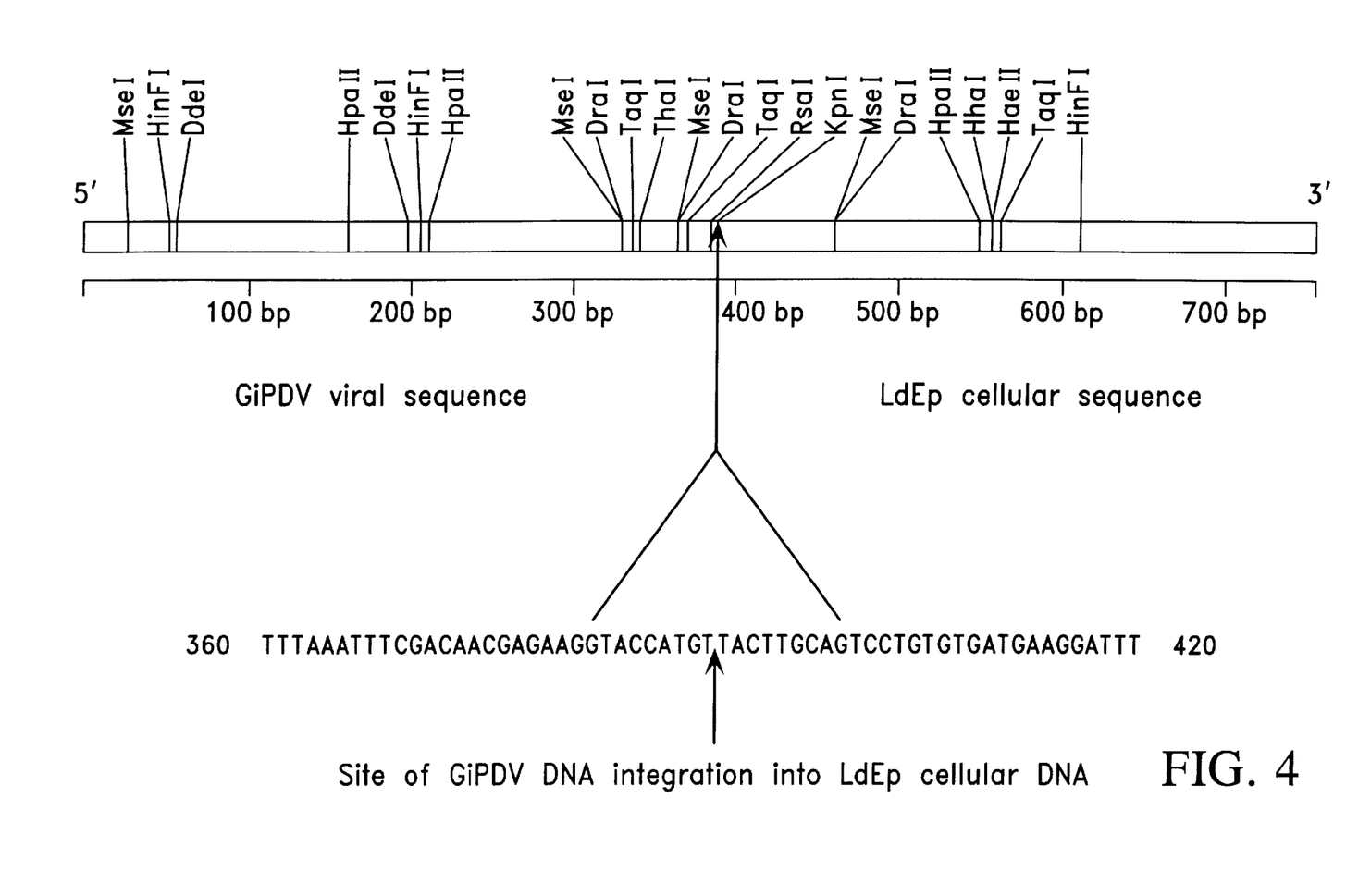
FIG. 4 shows a restriction map of clone pB17 containing a GiPDV viral/*L. dispar* cellular integration border. Site of integration was determined by probing Southern blot containing restriction digests of pB17 separately with GiPDV viral and LdEp cellular probes. Sequences around integration border are shown (SEQ ID NO: 5). Site of integration is indicated by an arrow and was determined by restriction mapping and comparison of border sequences to those of GiPDV viral DNA circular genomic DNA fragment known to integrate (clone p157).

In Southern blots, similar restriction patterns were obtained among the diverse infected insect cell lines using GiPDV-specific clone pTM145 as a probe (FIG. 1). In addition, PCR amplification produced similar length GiPDV sequences among the infected insect cell lines (FIG. 2), indicating that the same or a very similar portion(s) of the GiPDV genome was maintained in these cell lines. While it is possible that these GiPDV sequences are maintained in vitro in episomal fashion in the transformed insect cell lines described, it is believed that the GiPDV DNA is maintained integrated in the chromosomal DNA of transformed insect cell lines, based on evidence for GiPDV integration into the L. dispar cell line IPLB-LdEp chromosome. A sub-clone, p7-54, containing one viral/cellular integration border was isolated and restriction mapped (FIG. 3). A small (<900 bp) sub-clone, pB17, was obtained by sub-cloning the AluI fragment of p7-54 that contained the viral/cellular border. The sub-clone, pB17, was restriction mapped and sequenced, and the GiPDV viral and L. dispar cellular sequences determined (FIG. 4). Isolation of an integration border provided further proof of GiPDV DNA integration into L. dispar cellular DNA and provided necessary information regarding the sequence location within the L. dispar chromosome targeted for integration by GiPDV viral DNA. Because GiPDV restriction patterns are similar among transformed insect cell lines, the site for GiPDV integration within the chromosome of each insect cell line is likely similar.

Figure 5:
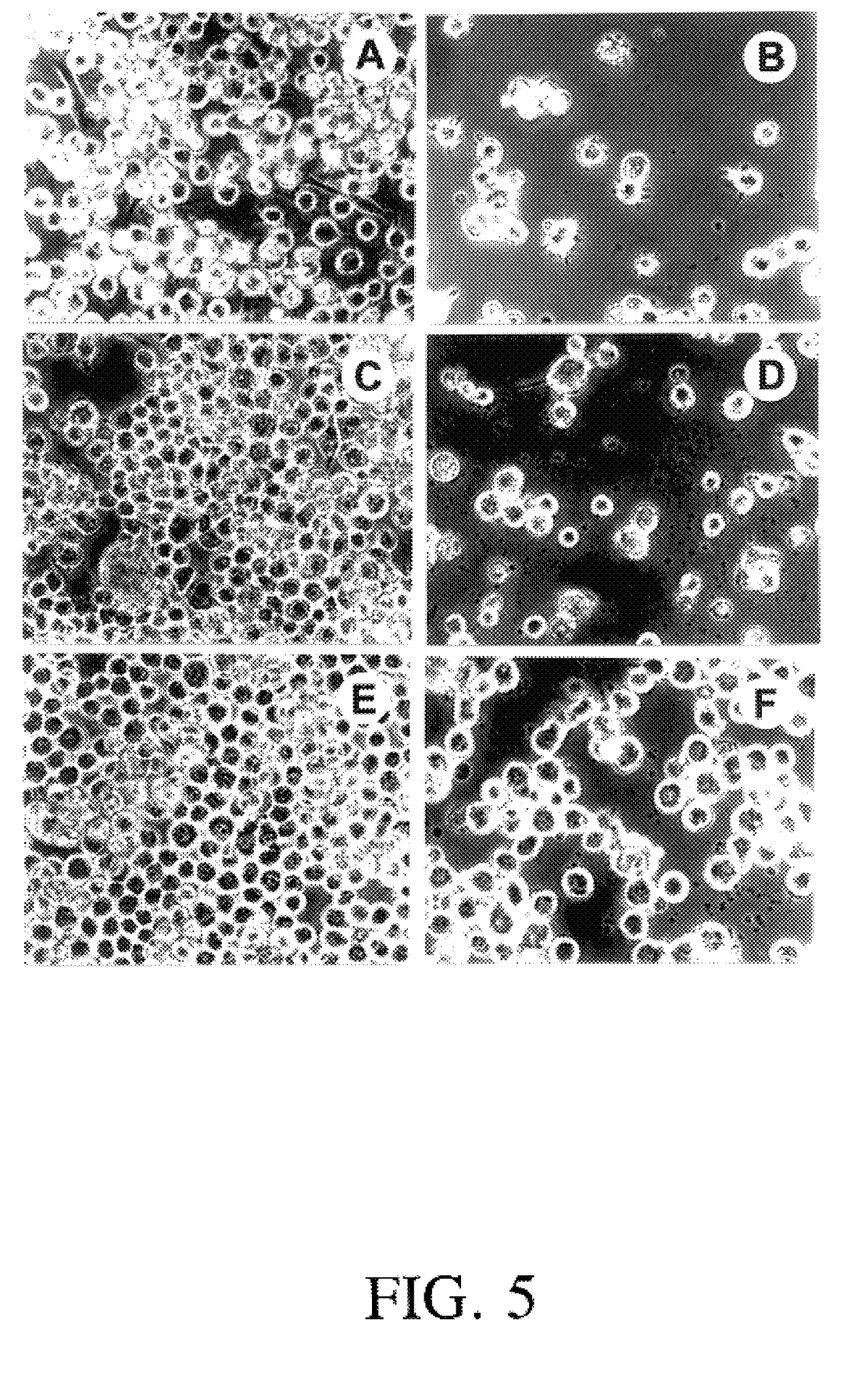
FIG. 5 shows *L. dispar* cell lines IPLB-Ld652Y uninfected (A) and infected (B) with GiPDV, IPLB-LdEp uninfected (C) and infected (D) with GiPDV, and IPLB-LdElta uninfected (E) and infected (F) with GiPDV, seven days post infection.

Initial studies to confirm transformation were carried out where L. dispar cell lines IPLB-Ld652Y, IPLB-LdEp and IPLB-LdEIta were infected with GiPDV obtained from the ovaries and the venom gland of a single G. indiensis. Infection of L. dispar cells with GiPDV (in the presence of venom) induced distinct, though temporary, changes in host cell morphology and growth rates (FIG. 5, B, D, and F) compared to uninfected cells (FIG. 5, A, C, and E). Infected cells formed aggregates not seen in uninfected cells. The division rate of the cells was greatly slowed compared to uninfected cells. These differences gradually faded during weekly passage of the cell lines, however, and by two months post infection, the growth rates of infected and uninfected cells were similar.

Figure 6:
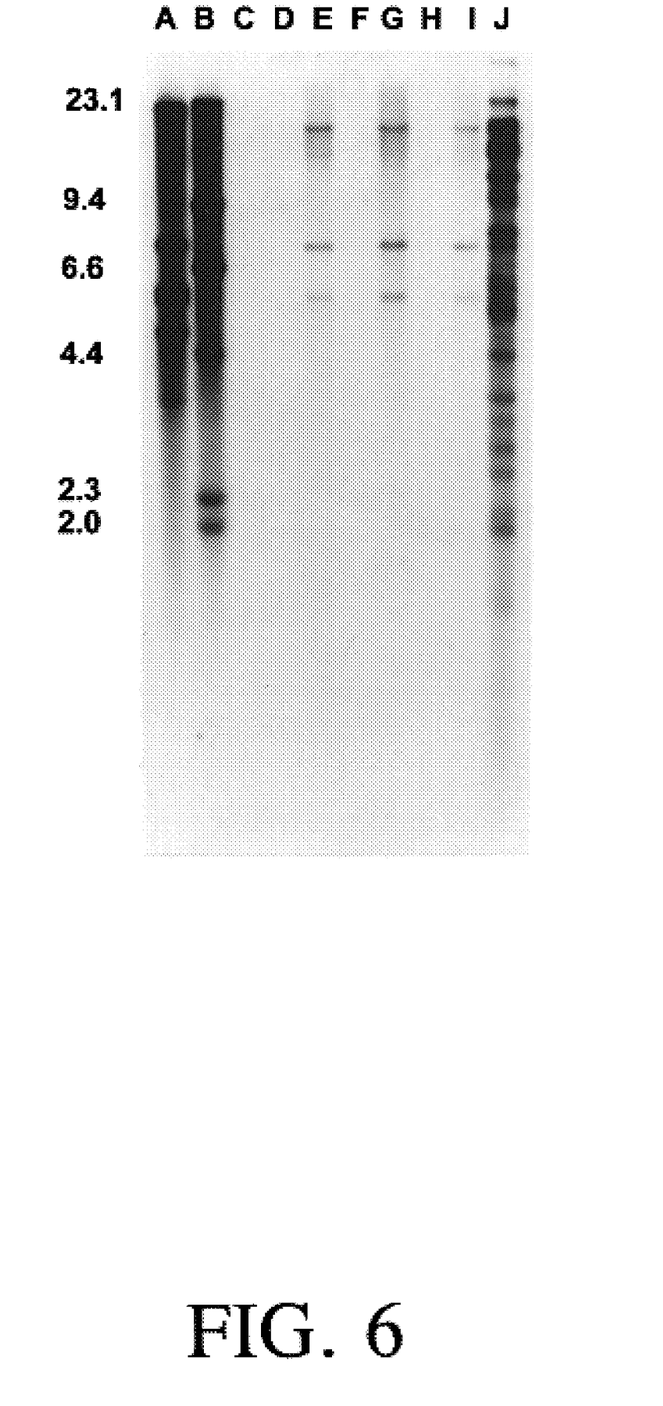
FIG. 6 shows Southern blot analysis of *L. dispar* cell lines transformed by infection with the *G. indiensis* polydnavirus.

The infected cells were analyzed for the presence of GiPDV viral sequences by extracting total nucleic acids, followed by Southern blots. No signal was detected from DNA of uninfected LdEp cells (FIG. 6, lanes D, F, H) when the Southern blots were probed with labeled total genomic GiPDV DNA. However, labeled GiPDV DNA hybridized to three prominent bands (approximate sizes of 15 kb, 7 kb and 5 kb) in BamHI digests of DNA extracted from infected cells after nine passages, or 60 days (FIG. 6, lanes E, G and I). Comparison of detected bands in this digest to BamHI digested GiPDV DNA (FIG. 6, lane J) indicated that only part of the total GiPDV genome was present in infected cells. Based on these restriction patterns, the portion of the GiPDV genome present in the infected cells appeared to be approximately 27 kb. Restriction patterns of HindIII digests and XbaI digests of DNA extracted from GiPDV infected cells also showed identical patterns in all three cell lines, and GiPDV DNA present in the cells totaled 25 to 27 kb. These results suggested that the same part of the GiPDV genome had been maintained in each cell line, although it was possible that the GiPDV DNA was present extrachromosomally. After weekly passage of the transformed cells (not selected) for over 175 passages (two and a half years), no significant change in restriction patterns was observed. Thus the GiPDV DNA appeared to be stably maintained.

Figure 7:
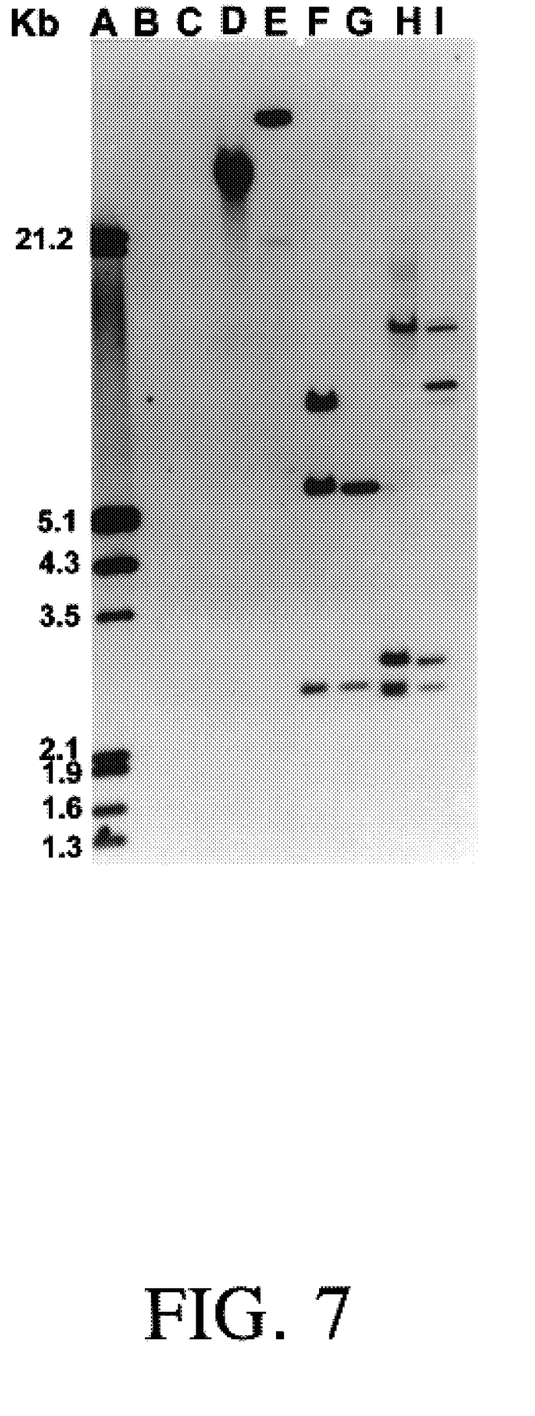

To determine whether GiPDV DNA was maintained integrated in the insect cell chromosome or was present extrachromosomally, hybridization experiments were carried out utilizing a viral clone, pTM145 (7.5 kb, one internal BamHI site), that hybridized specifically to transformed cellular DNA. A Southern blot of restriction-digested transformed and non-transformed IPLB-LdEp cellular DNAs and digested and uncut GiPDV DNA was probed with labeled pTM145 DNA (FIG. 7). The pTM145 DNA hybridized to DNA corresponding exactly to the chromosomal DNA from transformed cells (FIG. 7, Lane D) but not to DNA from non-transformed cells (FIG. 7, lane C). No bands were detected in transformed cells corresponding supercoiled or relaxed circular virus bands observed in undigested GiPDV DNA (FIG. 7, lane E). These results suggested that polydnavirus DNA maintained in transformed cells is integrated into the host genome and is not extrachromosomal. Clone pTM145 hybridized to only one segment of the multipartite GiPDV genome (FIG. 7), indicating that this single circular genome segment represents or contains the integrating DNA.

Figure 8:
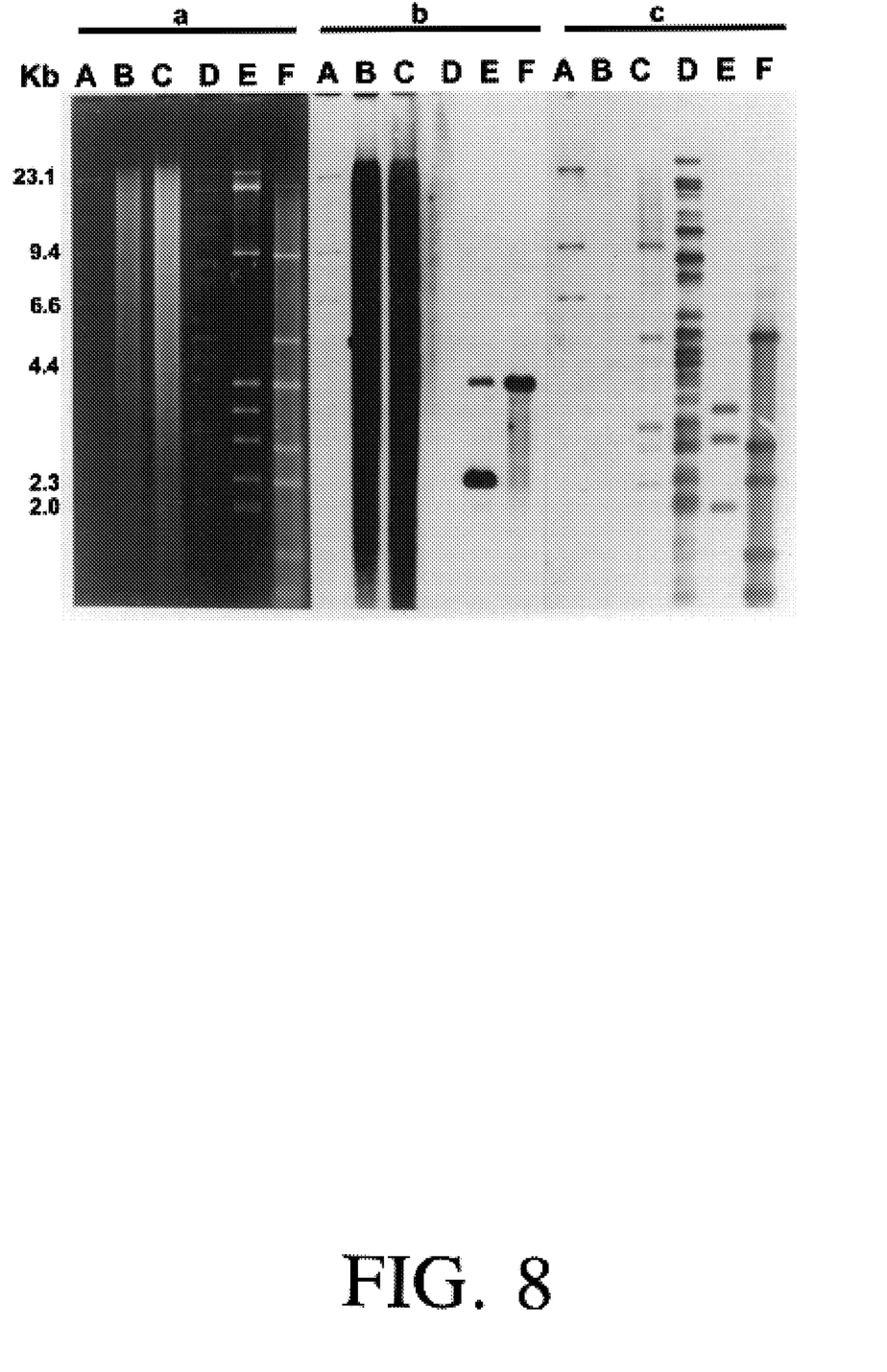
FIG. 8 shows Southern blot analysis of DNAs cloned from IPLB-LdEp cells infected with GiPDV. Lane B, DNAs isolated from non-transformed IPLB-LdEp cells; lane C, DNAs isolated from transformed IPLB-LdEp cells; lane D, DNAs isolated from GiPDV DNA from female wasps; lane E, DNAs isolated from clone E/G 12; lane F, DNAs isolated from clone E/G 25 were digested with EcoRI and electrophoresed through a 0.7% agarose gel (panel a). The DNAs were transferred to nylon membrane. Digoxigenin-labeled total DNA isolated from IPLB-LdEp cells (panel b) and GiPDV virus (panel c) were used as hybridization probes. Lane A contains molecular size standard as indicated by size in kilobase pairs.

To characterize the GiPDV genome segment involved in transformation of *L. dispar* cell lines a lambda phage library containing fragments of putatively transformed cellular (LdEp/Gi) DNA was constructed. Clones containing GiPDV or LdEp/Gi DNA were isolated by probing the library with labeled GiPDV DNA. Two clones derived from the transformed cell line (E/G 12 and E/G 25) clearly contained sequences from both GiPDV and insect cell genome as shown by reciprocal hybridization of EcoRI digests of clones E/G 12 and E/G 25 separately with labeled total GiPDV and IPLB-LdEp insect cell DNAs (FIG. 8).

Previous studies have determined that ichneumonid polydnavirus genome segments are integrated into the wasp genome [Fleming and Summers. 1990. In: *Molecular insect science*. (Hagedorn et al., eds.) pp. 99–105; Fleming, J. G. W. 1991. *Biological Control*. vol. 1, pp. 127–135; Fleming and Summers. 1986. *J. Virology*. vol. 57, pp. 552–562; Xu and Stoltz. 1991. *J. Virology*. vol 65, pp. 6693–6704], and the parasitoid viral markers routinely segregate in Mendelian fashion, suggesting vertical transmission (Stoltz, D. B. 1990. *J. Gen. Virol*. vol. 71, pp. 1051–1056). Polydnavirus DNA (but no polydnavirus particles) can be found in males and in female non-ovarian tissues, and males can transmit polydnaviruses to female offspring (Stoltz et al., 1986, supra). Although there is strong evidence for the chromosomal transmission of polydnavirus among wasp populations, extrachromosomal polydnavirus in these tissues has been detected (Fleming and Summers, 1990, supra; Stoltz et al., 1986, supra). The data shown here strongly suggest that part of the polydnavirus genome can integrate into the genome of an infected host.

As with *L. dispar* cell lines, infection of other lepidopteran and coleopteran cell lines with GiPDV derived from various tissues induced distinct, temporary changes in host cell morphology and growth rates as compared with uninfected cells. In all cell lines, infection with GiPDV slowed the cell division rate and caused cells to form aggregates not normally seen in uninfected cells. For all cell lines, the GiPDV-induced effects on cell growth and morphology gradually dissipated through weekly passage of the cell lines until the growth rates of uninfected and infected cells were similar.

Infected cells were analyzed for the presence of GiPDV viral sequences using labeled GiPDV clone pTM145 DNA as a probe (Example 7). No signal was detected from DNA of any uninfected cells when Southern-blotted, EcoRI-digested DNAs were probed with labeled PTM145 DNA (FIG. 1). Signal was detected from GiPDV DNA and GiPDV-infected cell line DNAs from the lepidopteran IPLB-LdEp/Gi, IPLB-SF21/Gi, IPLB-TN-$R^2$/Gi and IAL-PID2/Gi, and the coleopteran IPLB-DU182E/Gi (FIG. 1). No signal was detectable from GiPDV-infected mosquito cell line C7/10, and some GiPDV-infected cell lines (i.e. IPLB-SF21/Gi) hybridizied less strongly with the probe than others. The GiPDV sequences were stably maintained, as some GiPDV-infected insect cell lines had been maintained for over 250 passages in the laboratory at the time genomic DNA was extracted.

The PCR primer pairs, p157F1/R1 and p157F16/R16, were designed based on sequences of a cloned complete GiPDV genome segment for specific amplification of GiPDV sequences. This cloned GiPDV segment, p157, contained GiPDV DNA that was maintained in transformed cell lines and was from a different GiPDV genome segment than clone pTM145. GiPDV clone p157 was isolated from a library in which GiPDV DNA was inserted into the EcoRI site of the vector p5P64 (Promega Corp., Madison, Wis.) by electroporation using the method of Albrecht et al. (1994. *J. Gen. Virol*. vol. 75, pp. 3353–3363, herein incorporated by reference). GiPDV clone p157 was selected by dot hybridization using digoxigenin-labeled total GiPDV DNA, IPLB-LdEp cellular DNA, and IPLB-LdEp/Gi cellular DNA separately as probes. Clone p157 hybridized strongly with GiPDV and IPLB-LdEp/Gi probes and not at all with IPLB-LdEp probe. Clone p157 represents one complete circular segment of the GiPDV genome. Primer pairs p157F1/R1 and p157F16/R16 primed amplification of 1.9 kb and 2.8 kb DNA fragments, respectively, from GiPDV, positive control GiPDV clone p157, and from IPLB-LdEp/Gi, IPLB-TN-$R^2$/Gi, IPLB-SF21/Gi, IA-PID2/Gi, IPLB-DU182E/Gi and IPLB-HvT1 (weak) GiPDV-infected cell line DNAs (FIGS. 2A and 2B'). The primers also primed amplification of 1.9 kb and 2.8 kb DNA fragments from IPLB-Tcon1/Gi, IPLB-Tex2/Gi and IPLB-FB/Gi GiPDV-infected cell line DNAs. These GiPDV-specific primer pairs did not prime amplification from GiPDV-infected mosquito cell line C7/10 (FIGS. 2A and 2B, lane C7/10/Gi) or from any non-infected insect cell line DNA (FIGS. 2A and 2B').

The cells are transformed as described in Example 3 or Example 7 utilizing GiPDV DNA prepared as described in Example 1. Essentially, DNA is obtained by isolating calyx fluid containing polydnavirus which is capable of infecting insects from a female parasitoid wasp, adding the fluid containing polydnavirus to a culture of insect cells whereby the cells are infected, and incubating the cells for a time sufficient for DNA to be incorporated into the genome of the insect cells. Effective DNA(S) are segment(s) capable of integrating into the genome and are at least a circular fragment of approximately 18.5 kb. Polydnaviruses may be braconid or ichneumond polydnaviruses, in particular such as that from *G. indiensis*. Insect cells of particular interest are Lepidopteran or Coleopteran insect cells.

This polydnaviral system provides the basis for developing virus-derived transformation vectors. Currently the commonly-used baculovirus expression vector system has limitations because protein expression is transient, killing the host cells and necessitating extra bioreactors for producing viral inocula and insect cells for further infection. A polydnavirus-based shuttle vector system, however, would generate stably-transformed insect cells containing foreign genes of interest to be expressed in an inducible system.

The following examples are intended only to further illustrate the invention and are not intended to limit the scope of the invention as defined by the claims.

EXAMPLES

Example 1

Isolation of *Glytapanteles indiensis* Polydnavirus (GiPDV) DNA.

A female braconid *Glyptapanteles indiensis* parasitic wasp was dissected on a petri plate under dissecting microscope, the reproductive tract isolated and placed in a drop of TE (10 mM Tris/1 mM EDTA, pH 8) buffer. Fluid containing polydnaviruses was gently released from the calyx into the buffer by applying pressure to the calyx with dissecting forceps. The fluid was collected to an Eppendorf tube, and the polydnavirus DNA extracted by adding an equal volume of extraction buffer (0.02M Tris, pH 8, 0.04 M NaCl, 0.002 M $CaCl_2$) containing 500 µg/ml proteinase K and incubating 1 hour at 37° C. An equal volume of phenol/chloroform was added, the sample mixed, and centrifuged at 10K rpm for 10 min. The supernatant was precipitated in 2 vol 100% ethanol, and the polydnavirus nucleic acid pellet resuspended in TE buffer.

Example 2

Isolation of Clones of GiPDV DNA Capable of Persisting in *Lymantria dispar* Cells In Vitro.

Clone libraries were isolated from the GiPDV genome by two methods. A plasmid library of GiPDV DNA was generated by inserting restriction digested GiPDV DNA fragments into BamHI, EcoRI, HindIII, or XbaI restriction sites in pGEM7zf(+) vector (Promega Corporation, supra). A plasmid library was also generated by electroporation using the method of Albrecht et al., supra, in which GiPDV DNA fragments were inserted into EcoRI site of pSP64 vector (Promega Corp., supra). Individual clones that represented GiPDV DNA capable of persisting in infected gypsy moth cells in vitro were selected by dot hybridization at 48° C. using digoxigenin-labeled total GiPDV DNA, IPLB-LdEp cellular DNA, and IPLB-LdEp infected with GiPDV (IPLB-LdEp/Gi) DNA separately as probes. Clones which hybridized strongly with GiPDV and IPLB-LdEp/Gi probes and did not hybridize at all with the IPLB-LdEp probe were selected. Annealed DNAs were visualized by fluorography [Boehringer Mannheim Biochemicals (BMB), Indianapolis, Ind.].

Example 3

Generation of Cell Lines Infected with Polydnavirus.

*Lymantria dispar* cell lines IPLB-Ld652Y, IPLB-LdEp, and IPLB-LdEIta were infected with GiPDV from a single female braconid gypsy moth parasitoid *G. indiensis*. Two ovaries and the venom gland were aseptically dissected from a single female wasp and placed into one well of a 24-well dish containing 40–60% confluent IPLB-Ld652Y, IPLB-LdEp or IPLB-LdEIta cells in 0.5 ml ExCell 400 medium (JRH Biosciences, Lenexa, Kans.) supplemented with 25 µg per ml gentamicin. The organs were minced with forceps, releasing the calyx fluid and the venom, gently mixed, and incubated with cells at 27° C. Infected cells (shown in FIG. 5) were split normally as determined by the cell density.

Example 4

Analysis of Putatively Transformed *L. dispar* Cell Lines for GiPDV Sequences.

Total nucleic acids were extracted and analyzed by Southern blotting following digestion with either BamHI, HindIII or XbaI using digoxigenin-labeled GiPDV genomic DNA as a probe. Total genomic DNA was prepared from GiPDV infected and non-infected cells using standard techniques. Genomic DNA from each sample was digested then electrophoresed through a 0.7% agarose gel and transferred to nylon membrane (as described by 13). Digoxigenin-labeled total GiPDV DNA (BMB, supra) was used as a hybridization probe. Annealed DNAs were visualized by fluorography (BMB, supra). Results are shown in FIG. 6.

Example 5

Isolation of Clones from the IPLB-LdEp Cellular/GiPDV Viral Integration Border.

To isolate DNA clones containing both viral and cellular sequences, a lambda phage library was generated from IPLB-LdEp cells infected with GiPDV DNA as described. MboI-digested DNA fragments were inserted into the BamHI site of the Lambda Dash II vector (Stratagene, Inc. La Jolla, Calif.). Individual clones hybridizing to labeled GiPDV were isolated by plaque lift technique (Sambrook et al. 1989. *Molecular cloning: a laboratory manual*. Cold Spring Harbor Laboratory Press, Cold Spring Harvor, N.Y.). Clones were analyzed by restriction digestion and Southern hybridization (Southern, E. M. 1975. *J. Mol. Biol.* vol. 98, pp. 503–517) using digoxigenin-labeled (BMB, supra) total GiPDV and IPLB-LdEp DNA as probes. Results are shown in FIG. 3.

Example 6

Generation of Cell Lines Infected with Polydnavirus.

The insect cell lines listed in Table 1 were infected separately with GiPDV from a single braconid *G. indiensis* adult female, as described in Example 3. Briefly, two ovaries and the venom gland were dissected from a single wasp and placed into a well of a 24-well dish containing 40–60% confluent insect cells in 0.5 ml appropriate media listed in Table 1 (ExCell 400 and IPL-52B, JRH Biosciences, supra; TNM-FH and Eagles MEM, Gibco/BRL, Gaithersburg, Md.) with 25 µg/ml gentamicin. The calyx fluid and venom were released, mixed, and incubated with cells at 26° C. Infected cells were subcultured as determined by cell density.

Example 7

Analysis of Putatively Transformed Insect Cell Lines for GiPDV Sequences by Southern Blots.

Total genomic nucleic acids were extracted from each non-infected and GiPDV-infected (putatively transformed)

insect cell line, after at least 10 passages, as described in Example 4. Genomic DNA (5 µg) from each sample was digested separately with restriction endonuclease EcoRI (Gibco/BRL, supra), electrophoresed through a 0.8% agarose gel, and transferred to nylon membrane as described (Gruber et al., supra). Digoxigenin-labeled (BMB, supra) plasmid DNA from GiPDV clone pTM145 (McKelvey et al., supra) was used as a hybridization probe. Annealed DNAs were visualized by fluorography (BMB, supra). The temperature for hybridization was 40°. Results are shown in FIG. 1.

Example 9
Analysis of Putatively Transformed Insect Cell Line DNAs for GiPDV Sequences by Polymerase Chain Reaction (PCR).

Several oligonucleotide primer pairs were designed for PCR on the basis of GiPDV sequences determined by direct sequencing of parts of GiPDV clone p157. The oligonucleotide sequences of the designed primers were:

```
                                           SEQ ID NO: 1
p157F1:    5'-CTA CGT CTA GCT TCT CAA G-3'

SEQ ID NO: 2
p157R1:    5'-CAT GAT TAA TAC TGT AAC ATC-3'

SEQ ID NO: 3
p157F16:   5'-CTA CAA GAT ACA GGT CAA TC-3'

SEQ ID NO: 4
p157R16:   5'-GCG GTG ATG ACG TAG GTG AC-3'
```

For PCRs, total genomic nucleic acids extracted from GiPDV and each non-infected and GiPDV-infected cell line were diluted in sterile deionized water to a final concentration of 20 ng/µl. Each 50-µl PCR reaction was performed by standard protocol using AmpliTaq Gold (Perkin-Elmer Cetus, Norwalk, Conn.), 0.2 µM of each primer and 200 µM deoxynucleotide triphosphates. Thirty-five PCR cycles were conducted in an automated thermocycler (Hybaid, Teddington, United Kingdom). After a 10-minute initial enzyme activation at 94° C., the following parameters were used: 1-min (2-min for the first cycle) denaturation at 94° C., 2-min annealing at 55° C. and 3-min primer extension (10-min in final cycle at 72° C. Control tubes without template were included in each experiment as negative controls. PCR products were analyzed by electrophoresis through a 0.8% agarose gel followed by staining in ethidium bromide and visualization of DNA bands using a UV transilluminator. Results are shown in FIG. 2.

All references cited hereinabove are herein incorporated by reference.

TABLE 1

Insect cell lines.

| Cell Line | Origin | Derived From | Tissue |
|---|---|---|---|
| IPLB-LdEp IPLB-LdEp/Gi[a] | Lepidopteran | Lymantria dispar, gypsy moth | embryo |
| IPLB-LdFB IPLB-LdFB/Gi | Lepidopteran | Lymantria dispar, gypsy moth | larval fat body |
| IPLB-TN-R$^2$ IPLB-TN-R$^2$/Gi | Lepidopteran | Trichoplusia ni, cabbage looper | embryo |
| IPLB-SF-21 IPLB-SF-21/Gi | Lepidopteran | Spodoptera frugiperda, fall armyworm | pupae |
| IAL-PID2 IAL-PID2/Gi | Lepidopteran | Plodia interpunctella, Indian meal moth | imaginal wing disc |
| IPLB-HvT1 IPLB-HvT1/Gi | Lepidopteran | Heliothis virescens, tobacco budworm | testes |
| IPLB-DU182E IPLB-DU182E/Gi | Coleopteran | Diabrotica undecimpunctata, corn rootworm | embryo |
| IPLB-Tcon1 IPLB-Tcon1/Gi | Hymenopteran | Trichogramma confusum, trichogrammid wasp | egg |
| IPLB-Tex2 IPLB-Tex2/Gi | Hymenopteran | Trichogramma exiguum, trichogrammid wasp | egg |
| C7/10 C7/10/Gi | Dipteran | Aedes albopictus, mosquito | egg |

[a]Cell lines labeled "/Gi" were infected with GiPDV and passaged weekly.

We claim:

1. A method of transforming an insect cell line, said method comprising
   a) isolating calyx fluid containing braconid polydnavirus *Glyptapanteles indiensis* from a female parasitoid wasp capable of infecting insects:
   b) adding said polydnavirus-containing fluid to a culture of insect cells to infect the cells; and
   c) incubating the infected cells for a time sufficient for polydnavirus DNA to be incorporated into the genome of the insect cells.

2. The method of claim 1, wherein said cell line is Lepidopteran or Coleopteran.

3. A transformed insect cell, wherein the cell has been transformed with braconid polydnavirus *Glyptapanteles indiensis* DNA contained in calyx fluid isolated from a female parasitoid wasp capable of infecting insects, said calyx fluid comprising polydnavirus *Glyptapanteles indiensis* having DNA capable of stable integration into the genome of an insect cell.

4. The transformed insect cell of claim 3, wherein said cell is a Lepidopteran or Coleopteran cell.

* * * * *

UNITED STATES PATENT AND TRADEMARK OFFICE
CERTIFICATE OF CORRECTION

PATENT NO. : 6,143,565
DATED : November 7, 2000
INVENTOR(S) : Edward M. Dougherty, Terry A. McKelvey, Donald A. Stoltz, Dwight E. Lynn and Dawn E. Gundersen-Rindal It is certified that error appears in the above-identified patent and that said Letters Patent is hereby corrected as shown below:

ON THE TITLE PAGE

Item [73] Assignee should read --

DALHOUSIE UNIVERSITY, 6299 SOUTH STREET, HALIFAX, NOVA SCOTIA, CANADA    B3H 4H6

Signed and Sealed this

Eighth Day of May, 2001

Attest:

NICHOLAS P. GODICI

*Attesting Officer*    Acting Director of the United States Patent and Trademark Office